United States Patent
Iwase et al.

(10) Patent No.: US 11,046,630 B2
(45) Date of Patent: Jun. 29, 2021

(54) METHOD FOR PRODUCING 1-CHLORO-2,3,3,4,4,5,5-HEPTAFLUORO-1-PENTENE, AND COMPOSITION

(71) Applicant: AGC Inc., Tokyo (JP)

(72) Inventors: Takuya Iwase, Tokyo (JP); Satoshi Kawaguchi, Tokyo (JP); Hirokazu Takagi, Tokyo (JP)

(73) Assignee: AGC Inc., Tokyo (JP)

( * ) Notice: Subject to any disclaimer, the term of this patent is extended or adjusted under 35 U.S.C. 154(b) by 0 days.

(21) Appl. No.: 17/092,385

(22) Filed: Nov. 9, 2020

(65) Prior Publication Data

US 2021/0053896 A1 Feb. 25, 2021

Related U.S. Application Data

(63) Continuation of application No. PCT/JP2019/019161, filed on May 14, 2019.

(30) Foreign Application Priority Data

May 15, 2018 (JP) .............................. JP2018-093851

(51) Int. Cl.
  *C07C 17/389* (2006.01)
  *C07C 21/18* (2006.01)

(52) U.S. Cl.
  CPC ............ *C07C 21/18* (2013.01); *C07C 17/389* (2013.01)

(58) Field of Classification Search
  CPC .............................. C07C 17/389; C07C 21/18
  See application file for complete search history.

(56) References Cited

U.S. PATENT DOCUMENTS

2010/0162738 A1* 7/2010 Low ...................... C07C 17/389
                                                             62/101
2016/0347693 A1   12/2016 Fukushima et al.

FOREIGN PATENT DOCUMENTS

JP        2008-162985 A       7/2008
WO   WO 2015/125877 A1        8/2015
WO   WO-2019124219 A1 *   6/2019  ............. C07C 21/18

OTHER PUBLICATIONS

WO-2019124219-A1, English translation, Jun. 2019, pp. 1-16 (Year: 2019).*
International Search Report dated Aug. 13, 2019 in PCT/JP2019/019161 filed on May 14, 2019, 1 page.
Zapevalov et al., "α, α-Disubstituted polyfluoro-alkenes", Zhurnal Organicheskoi Khimii, (Russia), 1988, vol. 24, No. 8, pp. 1626-1633.

* cited by examiner

*Primary Examiner* — Medhanit W Bahta
(74) *Attorney, Agent, or Firm* — Oblon, McClelland, Maier & Neustadt, L.L.P.

(57) ABSTRACT

To produce, from a composition containing 1-chloro-2,3,3,4,4,5,5-heptafluoro-1-pentene and a substance that may cause problems in reliability and performance, 1-chloro-2,3,3,4,4,5,5-heptafluoro-1-pentene in which the content of the substance has been reduced. This method for producing 1-chloro-2,3,3,4,4,5,5-heptafluoro-1-pentene comprises bringing a composition containing 1-chloro-2,3,3,4,4,5,5-heptafluoro-1-pentene and at least one substance selected from the group consisting of water, 3,3,4,4,5,5-hexafluoro-1-pentyne, 1-chloro-3,3,4,4,5,5-hexafluoro-1-pentyne and an oxide, into contact with a solid adsorbent, to remove the substance from the composition.

15 Claims, No Drawings

METHOD FOR PRODUCING 1-CHLORO-2,3,3,4,4,5,5-HEPTAFLUORO-1-PENTENE, AND COMPOSITION

TECHNICAL FIELD

The present invention relates to a method for producing 1-chloro-2,3,3,4,4,5,5-heptafluoro-1-pentene in which the content of a substance that may cause problems in reliability and performance is reduced, and a composition containing the same.

BACKGROUND ART

A hydrochlorofluorocarbon (HCFC) presents adverse effects to the ozone layer, and therefore, its production is expected to be regulated. HCFC may be 3,3-dichloro-1,1,1,2,2-pentafluoropropane ($CF_3$—$CF_2$—$CHCl_2$, HCFC-225ca, hereinafter referred to as 225ca), 1,3-dichloro-1,1,2,2,3-pentafluoropropane ($CClF_2$—$CF_2$—$CHFCl$, HCFC-225cb, hereinafter referred to as 225cb), etc. Along with the regulation of HCFC, it is desired to develop a compound that replaces HCFC.

As a compound replacing HCFC, for example, 1-chloro-2,3,3,4,4,5,5-heptafluoro-1-pentene (CHCl=CF—$CF_2$—$CF_2$—$CF_2H$, HCFO-1437dycc, hereinafter referred to as 1437dycc) may be mentioned. 1437dycc has a small global warming potential (GWP) and is expected to be a compound suitable for applications such as a cleaning agent, a solvent, a refrigerant, a foaming agent, an aerosol, etc.

Non-Patent Document 1 discloses a method in which 2,2,3,3,4,4,5,5-octafluoro-1-pentanol (hereinafter referred to as (OFPO) is reacted with dichlorotriphenylphosphorane to obtain 5-chloro-1,1,2,2,3,3,4,4-octafluoropentane (HCFC-448occc, hereafter referred to as 448occc), and then, 448occc is reacted with sodium methoxide to dehydrofluorinate 448occc, thereby to obtain 1437dycc.

PRIOR ART DOCUMENT

Non-Patent Document

Non-Patent Document 1: Zhurnal Organicheskoi Khimii, (Russia), 1988, Vol. 24, No. 8, 1626-1633.

DISCLOSURE OF INVENTION

Technical Problem

The composition containing 1437dycc produced by the method of Non-Patent Document 1 or the like contains a substance other than 1437dycc. The substance may, for example, be a by-product, water or an impurity. Such a substance may sometimes cause various problems in reliability and performance when the above composition is used as a cleaning agent, a solvent, a refrigerant, a foaming agent or an aerosol. Therefore, it is preferred to minimize the amount of the above substance in the composition.

The present invention has been made from the above viewpoint, and has an object to provide a method for producing, from a composition containing 1437dycc and a substance that may cause problems in reliability and performance, 1437dycc in which the content of the above substance is reduced.

Solution to Problem

The present invention has the following embodiments.

[1] A method for producing 1-chloro-2,3,3,4,4,5,5-heptafluoro-1-pentene, which comprises bringing a composition containing 1437dycc and at least one substance selected from the group consisting of water, 3,3,4,4,5,5-hexafluoro-1-pentyne (CH≡$CCF_2CF_2CHF_2$), 1-chloro-3,3,4,4,5,5-hexafluoro-1-pentyne (CCl≡$CCF_2CF_2CHF_2$) and an oxide, in contact with a solid adsorbent, to remove the substance from the composition.

[2] The production method according to [1], wherein the solid adsorbent contains at least one member selected from the group consisting of activated carbon, zeolite, silica and alumina.

[3] The production method according to [1], wherein the composition contains water, and the solid adsorbent contains zeolite.

[4] The production method according to [1], wherein the composition contains at least one member selected from the group consisting of 3,3,4,4,5,5-hexafluoro-1-pentyne and 1-chloro-3,3,4,4,5,5-hexafluoro-1-pentyne, and the solid adsorbent contains at least one member selected from the group consisting of activated carbon and silica.

[5] The production method according to [1], wherein the composition contains an oxide, and the solid adsorbent is activated carbon or alumina.

[6] The production method according to [5], wherein the oxide is at least one member selected from the group consisting of 3-chloro-2-fluoro-2-(1,1,2,2,3,3-hexafluoropropyl)-oxirane, 2,2,3,3,4,4-hexafluorobutanoyl fluoride, formyl chloride, 1-chloro-2,3,3,4,4,5,5-heptafluoro-1-hydroperoxy-1-pentene (E), 1-chloro-2,3,3,4,4,5,5-heptafluoro-1-hydroperoxy-1-pentene (Z), 1-chloro-2,3,3,4,4,5,5-heptafluoro-5-hydroperoxy-1-pentene (E) and 1-chloro-2,3,3,4,4,5,5-heptafluoro-5-hydroperoxy-1-pentene (Z).

[7] The production method according to [2] or [3], wherein the zeolite is at least one member selected from the group consisting of zeolite 3A, zeolite 4A and zeolite 5A.

[8] The production method according to [2] or [4], wherein the activated carbon has a specific surface area of from 600 to 2,500 $m^2/g$, an average pore diameter of from 1.6 to 3.5 nm and a pore volume of from 0.25 to 1.5 mL/g.

[9] The production method according to [2] or [4], wherein the silica is porous synthetic silica gel, mesoporous silica or silica-alumina.

[10] The production method according to [2] or [5], wherein the alumina has a BET specific surface area of from 50 to 350 $m^2/g$, an average pore diameter measured by a nitrogen adsorption method of from 5 to 200 Å and a pore volume of from 0.1 to 0.8 mL/g.

[11] The production method according to any one of [1] to [10], wherein 5-chloro-1,1,2,2,3,3,4,4-octafluoropentane is dehydrofluorinated to produce the composition.

[12] A composition comprising 1437dycc and at least one substance selected from the group consisting of water, 3,3,4,4,5,5-hexafluoro-1-pentyne, 1-chloro-3,3,4,4,5,5-hexafluoro-1-pentyne and an oxide, wherein the amount of said water in the composition is at most 200 mass ppm.

[13] The composition according to [12], wherein the amount of 3,3,4,4,5,5-hexafluoro-1-pentyne in the composition is from 1 to 1,200 mass ppm.

[14] The composition according to [12] or [13], wherein the amount of 1-chloro-3,3,4,4,5,5-hexafluoro-1-pentyne in the composition is from 1 to 600 mass ppm.

[15] The composition according to any one of [12] to [14], wherein the amount of the oxide in the composition is from 1 to 100 mass ppm.

[16] The composition according to any one of [12] to [15], wherein the oxide in the composition is at least one member selected from the group consisting of 3-chloro-2-fluoro-2-(1,1,2,2,3,3-hexafluoropropyl)-oxirane, 2,2,3,3,4,4-hexafluorobutanoyl fluoride, formyl chloride, 1-chloro-2,3,3,4,4,5,5-heptafluoro-1-hydroperoxy-1-pentene (E), 1-chloro-2,3,3,4,4,5,5-heptafluoro-1-hydroperoxy-1-pentene (Z), 1-chloro-2,3,3,4,4,5,5-heptafluoro-5-hydroperoxy-1-pentene (E) and 1-chloro-2,3,3,4,4,5,5-heptafluoro-5-hydroperoxy-1-pentene (Z).

Advantageous Effects of Invention

According to the invention, it is possible that from a composition containing 1437dycc and at least one substance selected from the group consisting of water, 3,3,4,4,5,5-hexafluoro-1-pentyne, 1-chloro-3,3,4,4,5,5-hexafluoro-1-pentyne and an oxide, the above substance can be efficiently removed, and 1437dycc in which the content of the above substance is reduced, can be produced.

DESCRIPTION OF EMBODIMENTS

The definitions of terms and terminology in this specification are as follows.

With respect to a "halogenated hydrocarbon", in a case where the abbreviation of the compound is shown in parentheses after the compound name, it is represented by the abbreviation instead of the compound name, as the case requires.

With respect to a "compound having a double bond in the molecule and having an E-form and a Z-form", the E-form or the Z-form is shown by indicating (E) or (Z) at the end of the abbreviation of the compound. A compound having no indication of (E) or (Z) at the end of the abbreviation of the compound name, represents either the (E) form, the (Z) form, or a mixture of the (E) form and the (Z) form.

"At least one substance selected from the group consisting of water, 3,3,4,4,5,5-hexafluoro-1-pentyne, 1-chloro-3,3,4,4,5,5-hexafluoro-1-pentyne and an oxide group" may be referred to also as a "substance (X)", and a composition containing 1437dycc and the substance (X) may be referred to also as a "composition for purification". The substance (X) is a substance that may cause problems in reliability and performance.

The average particle diameter is, unless otherwise specified, a volume-based 50% average particle diameter D50 to be measured by a sieving method as specified in JIS Z8801.

The average pore diameter of the solid adsorbent is measured by a constant volume gas adsorption method, unless otherwise specified. As the adsorption gas used in the constant volume gas adsorption method, $N_2$, $CO_2$, $CH_4$, $H_2$, Ar or the like is used.

The specific surface area is measured by a gas adsorption method using $N_2$, $CO_2$, $CH_4$, $H_2$, Ar, etc., unless otherwise specified.

The expression "to" indicating a numerical range is a range including the lower limit value and the upper limit value. When the lower limit value and the upper limit value of the numerical range are the same unit, one of them may be omitted for simplification.

[Composition for Purification]

The composition for purification is not particularly limited so long as it is a composition containing 1437dycc and the substance (X). The composition for purification may contain other components other than 1437dycc and the substance (X). Other components are raw materials for producing 1437dycc such as 448occc, by-products produced in the production step of 1437dycc, etc. The composition for purification may be liquid or gas.

As the composition for purification, it is possible to employ, for example, a reaction product containing 1437dycc, which is obtainable by reacting various raw material components for the purpose of producing 1437dycc. That is, as will be described later, in a case where the reaction product obtainable by the production step of 1437dycc contains 1437dycc and the substance (X), this reaction product may be used as it is, as a composition for purification. Or, the composition after the reaction product is washed with water or alkali to remove acidic substances such as hydrogen fluoride and hydrogen chloride contained in the reaction product, may be used as a composition for purification.

1437dycc has a carbon-carbon double bond in its molecule that is easily decomposed by OH radicals in the atmosphere, has low flammability, has a small effect on the ozone layer, and has a small effect on global warming. Therefore, it is highly useful as a solvent or a working medium (a heat medium to be used for heat exchange, etc., a working medium to be used for a heat cycle system, etc.).

The method for producing 1437dycc, which comprises the step of removing the substance (X) from the composition for purification, may further comprise a step of producing a composition for purification containing 1437dycc. 1437dycc is obtainable, for example, by a dehydrofluorination reaction of 5-chloro-1,1,2,2,3,3,4,4-octafluoropentane (HCFC-448occc, 448occc) by a liquid phase reaction or a gas phase reaction. The dehydrofluorination reaction by a liquid phase reaction means dehydrofluorination of 448occc in a liquid state. The dehydrofluorination reaction by a gas phase reaction means dehydrofluorination of 448occc in a gas state.

1437dycc is obtainable, for example, by subjecting 448occc to a dehydrofluorination reaction in the presence of a base. In the presence of a base, the dehydrofluorination reaction may be carried out by either a liquid phase reaction or a gas phase reaction. The above reaction is represented by the following formula (1).

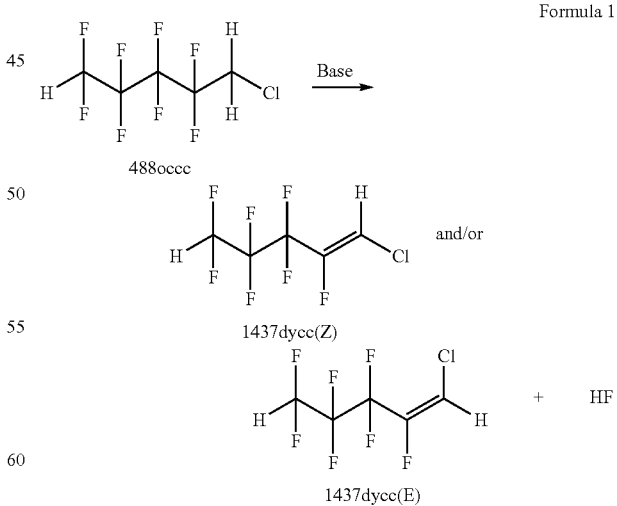

1437dycc(Z) has higher chemical stability than 1437dycc (E) and is more preferred as a solvent or a working medium. And, according to the method for producing 1437dycc in which 448occc is dehydrofluorinated in the presence of a base, 1437dycc can be efficiently produced. Further, according to the above production method, 1437dycc having a higher content ratio of 1437dycc(Z) than 1437dycc(E) can be obtained.

The base may be any base so long as it is capable of carrying out the dehydrofluorination reaction, and, for example, a metal hydroxide, a metal oxide and a metal carbonate may be mentioned. As the base, one type may be used alone, or two or more types may be used in combination.

Specific examples of the metal hydroxide include an alkali metal hydroxide and an alkaline earth metal hydroxide. Specific examples of the alkali metal hydroxide include lithium hydroxide, sodium hydroxide and potassium hydroxide. Specific examples of the alkaline earth metal hydroxide include magnesium hydroxide, calcium hydroxide, strontium hydroxide and barium hydroxide.

Specific examples of the metal oxide include an alkali metal oxide and an alkaline earth metal oxide. A specific example of the alkali metal oxide is sodium oxide. A specific example of the alkaline earth metal oxide is calcium oxide.

Specific examples of the metal carbonate include an alkali metal carbonate and an alkaline earth metal carbonate. Specific examples of the alkali metal carbonate include carbonates of lithium, sodium, potassium, rubidium, cesium and francium. Specific examples of the alkaline earth metal carbonate include carbonates of beryllium, magnesium, calcium, strontium, barium and radium.

In the case of dehydrofluorinating 448occc by a liquid phase reaction, the base is mixed with a solvent. As the solvent, for example, water is preferred. In the case where water is used, the base is preferably a metal hydroxide, more preferably potassium hydroxide or sodium hydroxide, from the viewpoints of high solubility in water, easy handling, and high reactivity.

In the case of dehydrofluorinating 448occc by a liquid phase reaction, it is preferred to carry out the dehydrofluorination reaction in the presence of a phase transfer catalyst in order to increase the reaction rate. The phase transfer catalyst may, for example, be mixed with a solvent.

Specific examples of the phase transfer catalyst include a quaternary ammonium salt, a quaternary phosphonium salt, a quaternary arsonium salt, a sulfonium salt and a crown ether. Among them, a quaternary ammonium salt, a quaternary phosphonium salt, a quaternary arsonium salt or a sulfonium salt is preferred, and a quaternary ammonium salt is more preferred from the viewpoint of excellent reaction rate.

Specific examples of the quaternary ammonium salt include tetra-n-butylammonium chloride (TBAC), tetra-n-butylammonium bromide (TBAB), methyl tri-n-octylammonium chloride (TOMAC), etc.

Specific examples of the quaternary phosphonium salt include tetraethylphosphonium, tetra-n-butylphosphonium, ethyl tri-n-octylphosphonium, cetyltriethylphosphonium, cetyl tri-n-butylphosphonium, n-butyltriphenylphosphonium, n-amyltriphenylphosphonium, methyltriphenylphosphonium, benzyltriphenylphosphonium, tetraphenylphosphonium, etc.

Specific examples of the quaternary arsonium salt include triphenylmethylarsonium fluoride, tetraphenylarsonium fluoride, triphenylmethylarsonium chloride, tetraphenylarsonium chloride, tetraphenylarsonium bromide, etc.

Specific examples of the sulfonium salt include di-n-butylmethylsulfonium iodide, tri-n-butylsulfonium tetrafluoroborate, dihexylmethylsulfonium iodide, dicyclohexylmethylsulfonium iodide, dodecylmethylethylsulfonium chloride, tris(diethylamino)sulfonium difluorotrimethyl silicate, etc.

Specific examples of the crown ether include 18-crown-6, dibenzo-18-crown-6, dicyclohexyl-18-crown-6, etc.

Among the above-mentioned phase transfer catalysts, TBAC, TBAB or TOMAC is preferable from the viewpoints of industrial availability, price, handling efficiency and reactivity.

The amount of the phase transfer catalyst is preferably from 0.01 to 10 parts by mass, more preferably from 0.05 to 5.0 parts by mass, further preferably from 0.1 to 2.0 parts by mass, particularly preferably from 0.1 to 1.0 part by mass, to 100 parts by mass of 448cccc. When the amount of the phase transfer catalyst is within the above range, it will be easy to obtain a sufficient reaction rate. If it is out of the above range, the reaction promoting effect tends to be hardly obtainable, and the cost tends to be disadvantageous. When the phase transfer catalyst is to be used, in order to make the phase transfer catalyst uniformly exist, it is preferred to mix the phase transfer catalyst with 448occc in advance and to supply it to the reactor in a mixed liquid state with 448occc. The amount of the phase transfer catalyst is most preferably from 0.1 to 0.8 part by mass to 100 parts by mass of 448occc, because the selectivity and yield of 1437dycc will be thereby high.

In the case of dehydrofluorinating 448occc in a gas phase reaction, for example, it is possible to dehydrofluorinate 448occc in the presence of activated carbon or a metal catalyst.

The specific surface area of the activated carbon is, from the viewpoint of improving the reaction conversion rate and inhibition of by-products, preferably from 10 to 3,000 $m^2/g$, more preferably from 20 to 2,500 $m^2/g$, further preferably from 50 to 2,000 $m^2/g$. The specific surface area of activated carbon is measured by a method based on the BET method.

Specific examples of the activated carbon include activated carbon prepared from charcoal, coal, coconut shell, etc. More specifically, formed coal having a length of about 2 to 5 mm, crushed coal, granular coal and powdered coal at a level of from about 4 to 50 mesh, etc. may be mentioned.

The activated carbon is preferably thoroughly dried before it is used in the reaction. From the viewpoint of improving reactivity and selectivity, the amount of water in the activated carbon is preferably at most 10 mass %, more preferably at most 5 mass %, further preferably at most 1 mass %, when the total amount of activated carbon and water is 100 mass %.

Specific examples of the metal catalyst include zero-valent iron, zero-valent cobalt, zero-valent nickel, zero-valent palladium, chromium oxide (chromia), aluminum oxide (alumina), zinc oxide, tin oxide, magnesium oxide, lanthanum oxide, nickel oxide, aluminum fluoride oxide, chromium fluoride oxide, magnesium fluoride oxide, lanthanum oxide fluoride, chromium hydroxide, an alkali metal halide and an alkaline earth metal halide.

In the case of dehydrofluorinating 448occc in a gas phase reaction, it is preferred to dehydrofluorinate it by using activated carbon or an alkaline earth metal fluoride from the viewpoint of improving reactivity and selectivity, and it is more preferred to dehydrofluorinate it by using activated carbon, $BaF_2$, $SrF_2$ or $CaF_2$.

(Composition for Purification)

The composition for purification may be one which contains 1437dycc even in a small amount, but the content of 1437dycc is preferably at least 50 mass %, more preferably at least 80 mass %, further preferably at least 90 mass %, to the total amount of the composition for purification. When the content of 1437dycc is at least the above lower limit value, the efficiency for removal of the substance (X) will be good. The contents of 1437dycc and substance (X) in the composition for purification are not particularly limited, but from the viewpoint of the efficiency for removal of the substance (X), the molar ratio represented by (substance (X))/(1437dycc) is preferably less than 1, more preferably from 0.001 to 0.7, further preferably from 0.1 to 0.2.

(Water)

In the composition for purification, for example, water used in the case of dehydrofluorinating 448occc by a liquid phase reaction, or water mixed at the time when a reaction product obtained by dehydrofluorinating 448occc is washed with water or an alkali, may sometimes be contained. Water may sometimes reduce the thermal and chemical stability of 1437dycc. From the viewpoint of the efficiency for removal of the substance (X), the content of water in the composition for purification is preferably at most 1 mass %, more preferably at most 0.5 mass %, further preferably at most 0.1 mass %.

(3,3,4,4,5,5-Hexafluoro-1-pentyne)

In the composition for purification, 3,3,4,4,5,5-hexafluoro-1-pentyne which is a by-product in the production step for 1437dycc by dehydrofluorinating 448occc, may sometimes be contained. 3,3,4,4,5,5-hexafluoro-1-pentyne is produced by progress of the dehydrofluorination reaction of 1437dycc represented by the following formula (2).

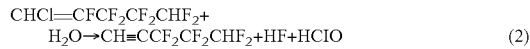

CHCl=CFCF$_2$CF$_2$CHF$_2$+H$_2$O→CH≡CCF$_2$CF$_2$CHF$_2$+HF+HClO  (2)

3,3,4,4,5,5-Hexafluoro-1-pentyne may sometimes reduce the thermal and chemical stability of 1437dycc. The content of 3,3,4,4,5,5-hexafluoro-1-pentyne in the composition for purification is preferably at most 1 mass %, more preferably at most 0.5 mass %, further preferably at most 0.2 mass %, to the total amount of the composition for purification, from the viewpoint of the efficiency for removal of the substance (X).

(1-Chloro-3,3,4,4,5,5-hexafluoro-1-pentyne)

In the composition for purification, 1-chloro-3,3,4,4,5,5-hexafluoro-1-pentyne which is produced as a by-product in the production step for 1437dycc by dehydrofluorinating 448occc, may sometimes be contained. 1-Chloro-3,3,4,4,5,5-hexafluoro-1-pentyne is produced by progress of the dehydrofluorination reaction of 1437dycc represented by the following formula (3).

CHCl=CFCF$_2$CF$_2$CHF$_2$→CCl≡CCF$_2$CF$_2$CHF$_2$+HF  (3)

1-Chloro-3,3,4,4,5,5-hexafluoro-1-pentyne may sometimes reduce the thermal and chemical stability of 1437dycc. The content of 1-chloro-3,3,4,4,5,5-hexafluoro-1-pentyne in the composition for purification is preferably at most 1 mass %, more preferably at most 0.5 mass %, further preferably at most 0.1 mass %, to the total amount of the composition for purification, from the viewpoint of the efficiency for removal of the substance (X).

(Oxide)

In the composition for purification, an oxide may sometimes be contained. The oxide may sometimes cause problems such as a decrease in stability of 1437dycc and formation of acidified substances. The oxide may, for example, be an oxide to be produced by the reaction of 1437dycc with oxygen.

Specifically, 3-chloro-2-fluoro-2-(1,1,2,2,3,3-hexafluoropropyl)-oxirane (oxide (A)) represented by the following formula (A), 2,2,3,3,4,4-hexafluorobutanoyl fluoride (oxide (B)) represented by the following formula (B), formyl chloride (oxide (C)) represented by the following formula (C), 1-chloro-2,3,3,4,4,5,5-heptafluoro-1-hydroperoxy-1-pentene (E) and 1-chloro-2,3,3,4,4,5,5-heptafluoro-1-hydroperoxy-1-pentene (Z) (oxide (D)) represented by the following formula (D), 1-chloro-2,3,3,4,4,5,5-heptafluoro-5-hydroperoxy-1-pentene (E) and 1-chloro-2,3,3,4,4,5,5-heptafluoro-5-hydroperoxy-1-pentene (Z) (oxide (E)) represented by the following formula (E), etc. may be mentioned.

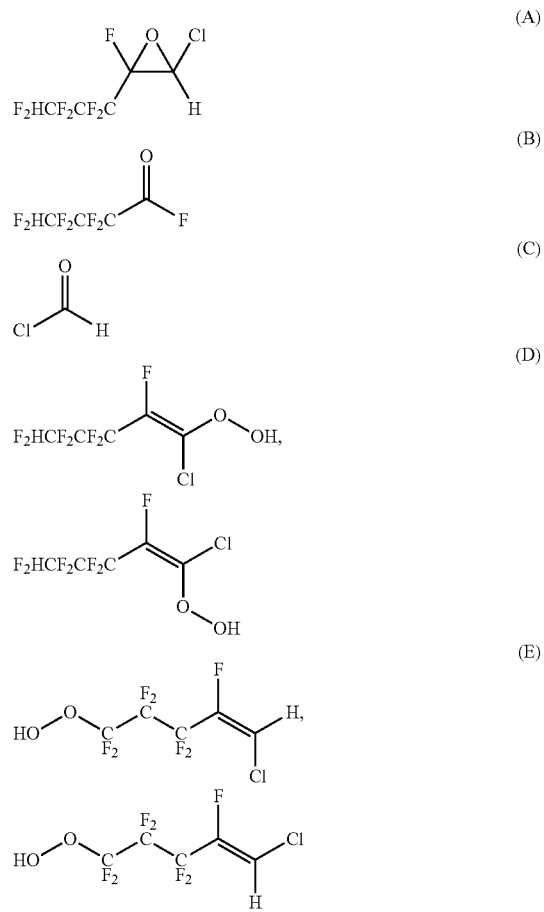

Oxide (A), oxide (B) and oxide (C) can be quantified by conducting analysis by using gas chromatography. The quantification of a hydroperoxide having an —O—O—H structure such as oxide (D) or oxide (E) is carried out by titration with sodium iodide and by back titration with sodium thiosulfate as shown in the following reaction formulae (4) and (5). ROOH represents oxide (D) or oxide (E), and ROH represents one in which the —O—O—H structure in oxide (D) or oxide (E) is changed to a —O—H structure.

ROOH+2NaI+H$_2$O→I$_2$+2NaOH+ROH  (4)

I$_2$+2Na$_2$S$_2$O$_3$→Na$_2$S$_4$O$_6$+2NaI  (5)

The above titration and back titration are conducted specifically as follows. To about 50 mL of a sample solution containing hydroperoxide, 2.5 mass % of sodium iodide (NaI) and about 40 mL of an acetone solution are mixed, and further about 50 mL of cold water is additionally mixed, whereby as shown by the above reaction formula (4), the mixture is colored yellow by the generated iodine ($I_2$). In a case where coloring does not occur at that time, hydroperoxide is judged to be below the detection limit. In the case of coloring, back titration of the mixed solution is conducted by a 0.01 mol/L (0.01N) sodium thiosulfate ($Na_2S_2O_3$) aqueous solution until the coloring disappears. The quantitative value of hydroperoxide is obtained by the following calculation formula using the experimental value of the above titration.

Hydroperoxide[mass ppm]={$Na_2S_2O_3$aqueous solution consumption[mL]×$Na_2S_2O_3$molar concentration[mol/mL]×(1/2)×ROOH molecular weight[g]}/sample solution weight[g]×10$^6$ The content of the oxide in the composition for purification is preferably at most 0.1 mass %, more preferably at most 0.05 mass %, further preferably at most 0.01 mass %, to the composition for purification, from the viewpoint of the efficiency for removal of the substance (X).

[Solid Adsorbent]

The solid adsorbent adsorbs at least one substance among the substances (X).

The solid adsorbent may be activated carbon, zeolite, silica, alumina, etc. As the solid adsorbent, one type may be used alone, or two or more types may be used in combination.

The solid adsorbent is preferably one heat-treated in advance by a dry gas at from 100° C. to 400° C. or heat-treated under reduced pressure, before being brought into contact with the composition for purification. It is thereby possible to improve the adsorption performance for the substance (X).

(Activated Carbon)

Activated carbon is, for example, activated carbon obtained by carbonizing and activating plant-based or fossil-based materials such as wood, wood flour, coconut shell, by-product during pulp production, bagasse, molasses, peat, lignite, brown coal, bituminous coal, anthracite, petroleum distillation residue components, petroleum pitch, coke, coal tar, etc.; various synthetic resins such as phenol resin, vinyl chloride resin, vinyl acetate resin, melamine resin, urea resin, resorcinol resin, celluloid, epoxy resin, polyurethane resin, polyester resin, acrylic resin, polyamide resin, etc.; synthetic rubbers such as polybutylene, polybutadiene, polychloroprene, etc.; or activated carbon raw materials such as synthetic wood and synthetic pulp. Among these activated carbon raw materials, coconut shell is preferably used, because it has a high adsorption performance for the substance (X).

The activated carbon is preferably one which has the following pore characteristics as measured by a nitrogen adsorption method at −196° C. (using ASAP2405 manufactured by Micromeritics Instrument Corporation) from the viewpoint of excellent adsorption performance for the substance (X). The specific surface area is preferably from 600 to 2,500 m$^2$/g, more preferably from 1,000 to 1,600 m$^2$/g, and the average pore diameter is preferably from 1.6 to 3.5 nm, more preferably from 1.7 to 2.0 nm. The pore volume is preferably from 0.25 to 1.5 mL/g, more preferably from 0.3 to 1.0 mL/g.

The activated carbon preferably has the following physical properties measured by the JIS K1474 test method from the viewpoint of excellent adsorption performance for the substance (X). The loss on drying is at most 5.0 mass %, preferably more than 0 mass % and at most 5.0 mass %, and the ignition residue is preferably at most 5.0 mass %. The packing density is preferably from 0.25 to 0.85 g/mL, more preferably from 0.35 g to 0.60 g/mL. The pH is preferably from 4.0 to 12.0, more preferably from 5.0 to 11.0. The acetone adsorption performance is preferably from 14.0 to 41.0 mass %, more preferably from 25.0 to 39.0 mass %. The iodine adsorption performance is preferably from 600 to 2,600 mg/g, more preferably from 900 mg/g to 1600 mg/g. The hardness is preferably from 90.0 to 100.0 mass %.

The shape of the activated carbon may be shaped carbon at a level of a length of from about 2 to 10 mm, crushed carbon, granular coal, etc. at a level of from about 4 to 50 mesh. From the viewpoint of activity, crushed coal with from 4 to 50 mesh, or shaped carbon with a length of from 2 to 5 mm, is preferred. Among them, from the viewpoint of economical advantage, crushed activated carbon is preferred, and crushed coconut shell activated carbon is particularly preferred. As the activated carbon, a commercially available product may be used, or activated carbon produced by a known method may be used. Further, as the activated carbon, one which has been subjected to pretreatment such as acid treatment, heat treatment, steam treatment, etc. may also be used.

(Zeolite)

The zeolite may, for example, be a synthetic zeolite having a chemical composition represented by the following formula (6) or (7).

$$K_xNa_y[(AlO_2)_{12}(SiO_2)_{12}] \cdot 27H_2O \quad (6)$$

(where x+y=12, and x:y=4:6 to 8:2).

$$K_xNa_y[(AlO_2)_{86}(SiO_2)_{106}] \cdot 276H_2O \quad (7)$$

(where x+y=86, and x:y=4:6 to 8:2).

Zeolites may, for example, be zeolites 3A, 4A and 5A. Zeolites 3A, 4A and 5A are synthetic zeolites having an average pore size of from 0.25 to 0.45 nm.

Zeolite 3A refers to a synthetic zeolite having an average pore size of 0.28±0.03 nm. However, due to the expansion and contraction, and kinetic energy, of the molecules that enter the cavities at normal operating temperature, the synthetic zeolite 3A may let molecules with an effective diameter of up to 0.3 nm be passed therethrough.

Zeolite 4A refers to a synthetic zeolite having an average pore size of 0.35±0.03 nm. Zeolite 5A refers to a synthetic zeolite having an average pore size of 0.42±0.03 nm.

As such zeolites, among A-type synthetic zeolites, those designated as 3A, 4A and 5A may be mentioned. Commercially available products may be molecular sieves 3A, 4A and 5A (trade name of Union Showa K.K.). As a commercially available X-type synthetic zeolite, molecular sieve 13X may be mentioned. In addition to zeolite 3A, 4A or 5A, molecular sieve 13X may be used in combination.

(Silica)

Silica is a compound having a chemical composition mainly of $SiO_2$. Silica may be porous synthetic silica gel, mesoporous silica, silica alumina, etc. As silica, one type may be used alone, or two or more types may be used in combination.

The shape of silica to be used as a solid adsorbent may be powder, fine particles, granules, thin films, etc. The shape of silica may be suitably selected depending on e.g. the adsorption process, etc. The shape of silica is preferably powder or fine particles from the viewpoint of the adsorption performance for the substance (X). Among them, fine particle silica may be uniformly dispersed in the liquid composition for purification to be in a state of a dispersion liquid, and thus is easy for handling. The fine particle silica easily forms an adsorption layer as described below in a reactor.

Porous synthetic silica gel is silica gel having pores. The shape of the porous synthetic silica gel may be a crushed non-spherical shape or a spherical shape, but a spherical shape is preferred from the viewpoint of high strength and being easy for recycling. The spherical shape is not limited to a true sphere and includes a slightly deformed spherical shape such as an elliptical sphere. The spherical shape has an average sphericity of preferably at least 0.5, more preferably at least 0.85.

The average particle diameter of the spherical porous synthetic silica gel is preferably from 0.1 to 10,000 μm, more preferably from 1 to 5,000 μm. The average pore diameter is preferably from 0.5 to 100 nm, more preferably from 2 to 50 nm. The specific surface area is preferably from 10 to 10,000 m$^2$/g, more preferably from 30 to 1,000 m$^2$/g. If out of these ranges, the content of effective particles or fine pores may decrease, which may lead to a decrease in the reaction rate, progress of side reactions, etc.

Porous synthetic silica gel is easily available as a commercial product, and may also be synthesized by a known method. Further, this porous synthetic silica gel may be subjected to pretreatment such as activation treatment. Commercially available products may, for example, be silica gel 40, silica gel 60, Wakosil C-200, Wakosil C-300 manufactured by Wako Pure Chemical Industries, and spherical silica gel manufactured by Kanto Chemical Co., Inc., which are often used as chromatographic carriers.

Mesoporous silica is an inorganic substance having uniform and regular mesopores (pores having a diameter of from 2 to 50 nm) and having a chemical composition mainly of SiO$_2$. The shape of mesoporous silica may be spherical, powder, fine particles, thin films, etc. Among them, spherical fine particles are more preferred, since they have a large specific surface area and high strength, are easy to be recycled, and can be easily industrially produced. The average pore diameter is preferably from 2 to 50 nm, more preferably from 2 to 10 nm. If the average pore size becomes to be smaller than 2 nm, the diffusion rate of the composition for purification into the mesoporous silica tends to be low, and the adsorption performance may be deteriorated. On the other hand, if the average pore diameter is larger than 50 nm, the composition for purification and the mesoporous silica may not be brought in sufficient contact with each other, and high selectivity and high yield may not be obtained.

The BET specific surface area of mesoporous silica is preferably from 10 to 3,000 m$^2$/g, more preferably from 50 to 3,000 m$^2$/g. The mesoporous silica having such a BET specific surface area can be easily produced, and can be efficiently in contact with the composition for purification to effectively adsorb the substance (X).

The average particle size of the mesoporous silica is preferably from 0.2 to 10,000 μm, more preferably from 1 to 5,000 μm.

Representative examples of mesoporous silica may be MCM-41, MCM-48, MCM-50, SBA-1, SBA-11, SBA-15, SBA-16, FSM-16, KIT-5, KIT-6, HMS (hexagonal), MSU-F, MSU-H, etc. These mesoporous silicas are commercially available and can also be synthesized by known methods.

Silica-alumina is a composite oxide containing silica (SiO$_2$) and alumina (Al$_2$O$_3$) as main components, and may be crystalline or amorphous. The total content of silica and alumina in the silica-alumina is preferably at least 95 mass %, and the content of silica is preferably at least 50 mol %.

The shape of silica-alumina may be spherical, powder, fine particles, thin films, etc. Among them, spherical fine particles are preferred, since they have a large specific surface area and high strength, are easy to be recycled and can be easily industrially produced.

The average particle size of the spherical fine particles of silica-alumina is preferably from 0.2 to 20,000 μm, more preferably from 1 to 10,000 μm. The average pore diameter is from 1 to 100 nm, preferably from 2 to 50 nm. The specific surface area is preferably from 10 to 10,000 m$^2$/g, more preferably from 30 to 1,000 m$^2$/g. The spherical fine particles of silica-alumina having the above average particle diameter and specific surface area can be easily produced. Further, when the average particle diameter and the specific surface area are as described above, the diffusion rate of the composition for purification will be high, and the adsorption performance for the substance (X) will be excellent.

Silica-alumina is easily available as a commercial product and can also be synthesized by a known method. Further, the silica-alumina may be one subjected to a pretreatment such as an activation treatment, as the case requires.

Commercially available products of silica-alumina may, for example, be silica-alumina 308 manufactured by Fuji Silysia Chemical Ltd., N633HN, N631HN, N633L, N631 L manufactured by JGC Catalysts and Chemicals Ltd., Al-MCM-41, Al-MSU-F manufactured by Sigma-Aldrich Co., etc.

(Alumina)

Alumina has a chemical composition mainly of Al$_2$O$_3$. As alumina, activated alumina is preferred. Activated alumina is an inorganic porous material and is a metastable phase alumina in the transition process from aluminum hydroxide to α-alumina which is a high temperature stable phase. The activated alumina is preferably amorphous or γ-alumina, since it has a large specific surface area and is excellent in adsorption performance.

The shape of the activated alumina is preferably a shaped body of e.g. spherical, cylindrical, prismatic, tablet-shaped, hollow cylindrical, honeycomb, etc. Granules having a particle diameter of from 3 mm to 8 mm are preferred from the viewpoint of handling efficiency and with a view to minimizing pressure loss during solid-gas contact.

The pores contained in activated alumina are classified into micropores (average pore diameter of at most 20 Å), macropores (average pore diameter of at least 500 Å), and mesopores located in the middle of both. Of these pores, ones to physically adsorb the substance (X) are the micropores, and the mesopores and the macropores are considered to relax the diffusion rate of the composition for purification. The pore volume occupied by the micropores is preferably within a range of from 10 to 50% of the total pore volume. The pore diameters and volumes of mesopores and macropores in activated alumina can be adjusted by adjusting the types of raw materials used for producing activated alumina and the molding conditions.

Activated alumina has, from the viewpoint of excellent adsorption performance for substance (X), a BET specific surface area of preferably from 50 to 350 m$^2$/g, more preferably from 100 to 350 m$^2$/g. The average pore diameter of the activated alumina measured by the nitrogen adsorption method is preferably from 5 to 200 Å, more preferably from 10 to 150 Å. The pore volume of activated alumina is preferably from 0.1 to 0.8 mL/g, more preferably from 0.2 to 0.5 mL/g.

(Method of Contacting Solid Adsorbent and Composition for Purification)

In the present invention, by bringing the composition for purification in contact with the above-described solid adsorbent, the substance (X) in the composition for purification will be adsorbed on the solid adsorbent and thus will be removed.

The composition for purification at the time of bringing it in contact with the solid adsorbent may be gas (gaseous) or liquid (liquid state). In the present invention, in a case where two or more solid adsorbents are used in combination, the order of the solid adsorbents to be contacted is not particularly limited. For example, the composition for purification may be contacted with two or more solid adsorbents sequentially in order, or may be simultaneously contacted e.g. by mixing two or more solid adsorbents. In the case where the solid adsorbents are contacted sequentially in order, with respect to the respective solid adsorbents to be used, the composition for purification and the solid adsorbents may be contacted by the contact methods as described later.

In the following, description will be made with reference to a method using a gaseous composition for purification. In this method, for example, a solid adsorbent is filled in a reactor to form an adsorption layer, and by circulating a gaseous composition for purification in the adsorption layer, it is possible to contact the solid adsorbent and the composition for purification. The contact between the solid adsorbent and the composition for purification by this method may be a batch system (batch system) or a continuous system.

The packing density of the solid adsorbent in the adsorption layer is preferably at least 0.1 g/cm$^3$, more preferably at least 0.25 g/cm$^3$. When the packing density is at least the lower limit value, the packing amount of the solid adsorbent per unit volume increases, and the processing amount of the gaseous composition for purification can be increased, so that the removal efficiency for the substance (X) other than 1437dycc will be improved. The number of adsorption layers may be one, or two or more. In a case where there are two or more adsorption layers, the adsorption layers may be in parallel or in series.

The temperature of the adsorption layer at the time of contact is preferably from 60 to 100° C., which is higher than the boiling point of 1437dycc, more preferably from 70 to 90° C., in order to maintain the composition for purification in a gas state. When the temperature of the adsorption layer is at least the lower limit value, the efficiency of removing the substance (X) by the solid adsorbent will be improved. When the temperature of the adsorption layer is at most the upper limit value, energy required for cooling the composition after purification will be less, and equipment, etc. may be simplified.

The pressure (absolute pressure) in the reactor at the time of contact is preferably from 10 to 500 kPa, more preferably from 90 to 300 kPa. When the pressure is at least the lower limit value, the handling efficiency will be good, and the equipment, etc. may be simplified. When the pressure is at most the upper limit value, the efficiency of removing the substance (X) will be improved.

The contact time between the gaseous composition for purification to be passed through the adsorption layer and the adsorption layer, is preferably from 1 to 1,000 seconds, more preferably from 3 to 300 seconds. When the contact time is at least the lower limit value, the efficiency for removing the substance (X) will be improved. When the contact time is at most the upper limit value, the adsorption layer used for purifying the composition for purification may be small, so that equipment, etc. may be simplified. In the method of circulating the composition for purification in the adsorption layer, the contact time corresponds to the residence time of the composition for purification in the reactor, and can be controlled by adjusting the supply amount (flow rate) of the composition for purification to the reactor. The same applies in the case of using a liquid composition for purification as described later.

From the viewpoint of removal efficiency, the total amount of the substance (X) contained in the gaseous composition for purification to be passed through the adsorption layer is preferably at most 0.05 part by mass, more preferably at most 0.02 part by mass, to 1 part by mass of the solid adsorbent in the adsorption layer. That is, in the method using the gaseous composition for purification, the amount of the gaseous composition for purification to be brought into contact with the solid adsorbent is preferably adjusted so that the ratio of the substance (X) to the solid adsorbent will be at most the above upper limit value.

The reactor to be used for contacting the composition for purification gas with the solid adsorbent may be any reactor that can be filled with the solid adsorbent to form an adsorption layer. The material of the reactor may, for example, be glass, iron, nickel or alloys containing these as main components, a fluororesin such as tetrafluoroethylene-perfluoro(alkyl vinyl ether) copolymer (PFA), etc.

Next, a method of using a liquid composition for purification will be described. In this method, in the same manner as in the case of using the gaseous composition for purification, a method in which an adsorption layer is formed in the reactor and the liquid composition for purification is circulated in the adsorption layer, may be used. A method may be used in which the solid adsorbent is immersed in the composition for purification in a reactor containing the solid adsorbent, and, as the case requires, mixed and stirred. The contact between the solid adsorbent and the composition for purification by such methods may be a batch system (batch system) or a continuous system.

When the composition for purification is brought in contact with the solid adsorbent in the liquid state, the composition for purification may be adjusted to a temperature not higher than the boiling point under normal pressure to be in the liquid state. The composition for purification may be dissolved in a solvent to be in the liquid state. As the solvent to be used at that time, by using a solvent having a boiling point different from that of 1437dycc, the solvent can be easily removed from the composition after purification by a method such as distillation.

The temperature in the reactor at the time of contact between the solid adsorbent and the composition for purification is preferably from −30° C. to 70° C., more preferably from 10° C. to 40° C. When the temperature is at least the lower limit value, the removal rate of impurities other than 1437dycc will be improved. When the temperature is at most the upper limit value, energy required to cool the composition after purification will be less, and the equipment, etc. may be simplified.

The pressure (gauge pressure) in the reactor at the time of contact between the solid adsorbent and the composition for purification is preferably from 0 to 200 kPa, more preferably from 100 to 150 kPa. When the pressure is at least the lower limit value, the removal rate of impurities other than 1437dycc will be improved. When the pressure is at most the upper limit value, handling efficiency will be good, and the equipment, etc. may be simplified.

In the method of circulating the composition for purification containing 1437dycc in the adsorption layer, the contact time between the liquid composition for purification flowing in the adsorption layer and the adsorption layer is preferably from 1 second to 1,000 seconds, more preferably from 3 seconds to 300 seconds. When the contact time is at least the lower limit value, the efficiency for removing the substance (X) will be improved. When the contact time is at most the upper limit value, the adsorption layer to be used for purifying the composition may be small, and the equipment, etc. may be simplified.

The preferred embodiments of the packing density of the solid adsorbent in the adsorption layer and the construction of the adsorption layer are the same as in the method using the gaseous composition for purification.

In the method of immersing the solid adsorbent in the composition for purification in the reactor containing the solid adsorbent, the contact time between the liquid composition for purification and the solid adsorbent in the reactor is preferably from 1 to 100 hours, more preferably from 3 to 60 hours. When the contact time is at least the lower limit value, the efficiency for removing the substance (X) will be improved. When the contact time is at most the upper limit value, the amount of the solid adsorbent to be used for purifying the composition for purification may be small, and the equipment, etc. may be simplified.

In the method of immersing the solid adsorbent in the composition for purification in the reactor, after the purification of the composition for purification, the purified composition and the solid adsorbent may be separated by sedimentation or filtration.

From the viewpoint of improving the efficiency for removal of the substance (X), the total amount of the substance (X) contained in the liquid composition for purification to be brought into contact with the solid adsorbent is at most 0.05 part by mass, more preferably at most 0.02 part by mass, to 1 part by mass of the solid adsorbent. That is, in the method using a liquid composition for purification, the liquid amount of the composition for purification to be brought in contact with the solid adsorbent is preferably adjusted so that the ratio of the substance (X) to the solid adsorbent becomes to be at most the above upper limit value.

The reactor to be used for contacting the liquid composition for purification with the solid adsorbent may, for example, be one capable of accommodating the solid adsorbent or one capable of forming an adsorption layer made of the solid adsorbent. The material of the reactor may, for example, be glass, iron, nickel, or alloys containing these as main components, a fluororesin such as a tetrafluoroethylene-perfluoro(alkyl vinyl ether) copolymer (PFA), etc. The reactor for mixing and contacting the mixed liquid with the solid adsorbent may be a reactor capable of contacting the solid adsorbent with the composition for purification in a liquid state at a desired temperature and pressure, such as an autoclave.

(Composition after Purification)

With respect of a solid adsorbent, in general, compounds that may be easily adsorbed, are different, depending on the composition of the composition to be purified and the type of the solid adsorbent (substance composition or pore size). In the present invention in which a composition containing 1437dycc and the substance (X) is an object to be purified, for example, water is easily adsorbed on zeolite, preferably zeolite 3A or zeolite 4A. Therefore, in the present invention, zeolite (particularly, zeolite 3A or 4A) is used as a solid adsorbent, and by contacting it with a composition for purification containing 1437dycc and water, water in the composition is selectively removed, to purify 1437dycc.

The oxide in the composition for purification is easily adsorbed on activated carbon or alumina. Therefore, in the production method of the embodiment, activated carbon or alumina is used as the solid adsorbent, and by contacting it with a composition for purification containing 1437dycc and an oxide, the oxide may be selectively removed to produce 1437dycc.

3,3,4,4,5,5-hexafluoro-1-pentyne or 1-chloro-3,3,4,4,5,5-hexafluoro-1-pentyne in the composition for purification is easily adsorbed on activated carbon or silica. Therefore, by using activated carbon or silica as a solid adsorbent, by contacting it with the composition for purification containing 1437dycc and 3,3,4,4,5,5-hexafluoro-1-pentyne or 1-chloro-3,3,4,4,5,5-hexafluoro-1-pentyne, 3,3,4,4,5,5-hexafluoro-1-pentyne or 1-chloro-3,3,4,4,5,5-hexafluoro-1-pentyne may be efficiently removed to produce 1437dycc.

As described above, in the present invention, by using one type of the solid adsorbent alone or two or more types of the solid adsorbent in combination, among the substances (X) contained in the composition for purification, the desired compounds can be removed at desired levels.

According to the present invention, by removing the substances (X) contained in the composition for purification, it is possible to obtain a composition having a reduced content of the substances (X).

The content of 1437dycc in the composition after purification according to the present invention can be made to be at least 90 mass %, and further can be made to be at least 95 mass %.

The content of water in the composition after purification according to the present invention can be made to be at most 200 mass ppm, further can be made to be at most 100 mass ppm, and particularly can be made to be at most 20 mass ppm. From the viewpoint of suppressing the production cost, the content of water in the composition after purification is preferably at least 1 mass ppm, more preferably at least 5 mass ppm.

The content of 3,3,4,4,5,5-hexafluoro-1-pentyne in the composition after purification according to the present invention can be made to be at most 1,200 mass ppm, and further can be made to be at most 1,100 mass ppm. The content of 3,3,4,4,5,5-hexafluoro-1-pentyne in the composition after purification is preferably at least 1 mass ppm. Within the above range, the production cost can be suppressed, and the stability of 1437dycc will be excellent.

The content of 1-chloro-3,3,4,4,5,5-hexafluoro-1-pentyne in the composition after purification according to the present invention can be made to be at most 600 mass ppm, further can be made to be at most 550 mass ppm, and particularly can be made to be at most 100 ppm. The content of 1-chloro-3,3,4,4,5,5-hexafluoro-1-pentyne in the composition after purification is preferably at least 1 mass ppm, more preferably at least 10 mass ppm, further preferably at least 50 mass ppm. Within the above range, the production cost can be suppressed, and the stability of 1437dycc will be excellent.

The total content of oxides in the composition after purification of the present invention can be made to be at most 100 mass ppm, further can be made to be at most 50 mass ppm, and particularly can be made to be at most 10 mass ppm. When the content of the oxides is at most the above upper limit vale, it is possible to sufficiently prevent the stability of the solvent composition from being lowered. When the content of oxides is at most the above upper limit value, it may not be reduced to the limit of 0 mass ppm. Here, the content of oxides in the composition for purification is preferably at least 1 mass ppm, more preferably at least 2 mass ppm. When it is at least the above lower limit value, oxidation of 1437dycc will be suppressed, and the stability of the solvent composition will be excellent.

EXAMPLES

In the following, the present invention will be described with reference to Examples, but the present invention is not limited to these Examples.

(Analytical Methods)

The contents (content ratios) of components other than water in the composition to be analyzed were analyzed by gas chromatography. As the column, DB-1301 (length 60 m×inner diameter 250 μm×thickness 1 μm, manufactured by Agilent Technologies Inc.) was used. The content of water was analyzed by a Karl Fischer moisture meter.

Using the analysis results of the above gas chromatography and Karl Fischer moisture meter, the proportion (mass ppm) of 3,3,4,4,5,5-hexafluoro-1-pentyne, the proportion (mass ppm) of 1-chloro-3,3,4,4,5,5-hexafluoro-1-pentyne and the proportion (mass ppm) of water, to the total amount of the composition to be analyzed, were obtained.

Production Example: Production of 1437Dycc

In a flask, 797 g of 448occc and 8.4 g of tetra-n-butylammonium bromide were put, and while the reaction temperature was kept at 25° C., 1,001 g of a 34 mass % potassium hydroxide aqueous solution was dropwise added over 1 hour. Then, the reaction was continued for 12 hours, so that the organic phase and the aqueous phase were separated into two phases, and the organic phase was recovered. The recovered organic phase was washed with an equal weight of water to obtain a composition (composition for purification) containing 1437dycc, water, 3,3,4,4,5,5-hexafluoro-1-pentyne and 1-chloro-3,3,4,4,5,5-hexafluoro-1-pentyne. The composition of the composition for purification is shown in Table 1.

Example 1

5 g of the composition for purification obtained by the above Production Example was placed in a 10 mL glass container with a lid, and to 5 g of the composition for purification, 10 mass % of activated carbon (product name: DIA Soap G4-8, manufactured by Mitsubishi Chemical Industries, Ltd.) was added, and then, the mixture was left to stand at room temperature for 48 hours. After 48 hours, the activated carbon was separated from the composition for purification, and the composition was analyzed, whereby the composition after treatment was as shown in Table 1.

Example 2

A treatment was conducted in the same manner as in Example 1 except that instead of the activated carbon, activated alumina (product name: activated alumina KHO_47, manufactured by Nishio Kogyo Co., Ltd.) was used. After the treatment, activated alumina was separated from the composition for purification, and the composition was analyzed, whereby the composition after treatment was as shown in Table 1.

Example 3

A treatment was conducted in the same manner as in Example 1 except that instead of the activated carbon, silica gel (trade name: Silica Gel 60N (spherical, neutral), manufactured by Kanto Chemical Co., Inc.) was used. After the treatment, silica gel was separated from the composition for purification, and the composition was analyzed, whereby the composition after treatment was as shown in Table 1.

Example 4

A treatment was conducted in the same manner as in Example 1 except that instead of the activated carbon, zeolite 3A (trade name: MS3A for chemicals, manufactured by Junsei Chemical Co., Ltd.) was used. After the treatment, zeolite 3A was separated from the composition for purification, and the composition was analyzed, whereby the composition after treatment was as shown in Table 2.

Example 5

A treatment was conducted in the same manner as in Example 1 except that instead of the activated carbon, zeolite 4A (trade name: MS4A for chemicals, manufactured by Junsei Chemical Co., Ltd.) was used. After the treatment, zeolite 4A was separated from the composition for purification, and the composition was analyzed, whereby the composition after treatment was as shown in Table 2.

Example 6

A treatment was conducted in the same manner as in Example 1 except that instead of the activated carbon, zeolite 5A (trade name: MS5A for chemicals, manufactured by Junsei Chemical Co., Ltd.) was used. After the treatment, zeolite 5A was separated from the composition for purification, and the composition was analyzed, whereby the composition after treatment was as shown in Table 2.

TABLE 1

| Compound name | Unit | Composition for purification | Example 1 Activated carbon | Example 2 Alumina | Example 3 Silica gel |
|---|---|---|---|---|---|
| | | | Composition after treatment | | |
| 1437dycc(Z) | mass % | 97.1 | 97.8 | 97.6 | 97.8 |
| 1437dycc(E) | mass % | 1.04 | 1.02 | 1.03 | 1.01 |
| Water | mass ppm | 333 | 410 | 262 | 373 |
| 3,3,4,4,5,5-Hexafluoro-1-pentyne | mass ppm | 1243 | 1072 | 1168 | 1034 |
| 1-Chloro-3,3,4,4,5,5-hexafluoro-1-pentyne | mass ppm | 632 | 502 | 573 | 532 |

TABLE 2

| Compound name | Unit | Composition for purification | Example 4 Zeolite 3A | Example 5 Zeolite 4A | Example 6 Zeolite 5A |
|---|---|---|---|---|---|
| | | | Composition after treatment | | |
| 1437dycc(Z) | mass % | 97.1 | 97.2 | 97.6 | 97.6 |
| 1437dycc(E) | mass % | 1.04 | 1.03 | 1.03 | 1.04 |
| Water | mass ppm | 333 | 1.00 | 0.00 | 2.00 |

TABLE 2-continued

| Solid absorbent | | | Example 4 | Example 5 | Example 6 |
|---|---|---|---|---|---|
| Compound name | Unit | Composition for purification | Zeolite 3A | Zeolite 4A | Zeolite 5A |
| | | | Composition after treatment | | |
| 3,3,4,4,5,5-Hexafluoro-1-pentyne | mass ppm | 1243 | 1162 | 1161 | 1207 |
| 1-Chloro-3,3,4,4,5,5-hexafluoro-1-pentyne | mass ppm | 632 | 601 | 584 | 585 |

From Examples 1 to 6, it is evident that by bringing the composition for purification containing 1437dycc in contact with activated carbon, alumina, silica gel, zeolite 3A, zeolite 4A or zeolite 5A, respectively, it is possible to remove TBAB, water, 3,3,4,4,5,5-hexafluoro-1-pentyne and 1-chloro-3,3,4,4,5,5-hexafluoro-1-pentyne from the composition for purification.

In particular, it is evident that for the removal of water from the composition for purification, the effects are high when zeolite 3A, zeolite 4A, or zeolite 5A is used, and for the removal of 3,3,4,4,5,5-hexafluoro-1-pentyne and 1-chloro-3,3,4,4,5,5-hexafluoro-1-pentyne, the effects are high when activated carbon or silica gel is used.

INDUSTRIAL APPLICABILITY

The composition containing 1437dycc to be produced according to the present invention has a reduced content of substances that may cause problems in reliability and performance, and thus can be advantageously used in a wide range of fields such as cleaning agents, solvents, refrigerants, foaming agents, aerosols, etc.

This application is a continuation of PCT Application No. PCT/JP2019/019161, filed on May 15, 2019, which is based upon and claims the benefit of priority from Japanese Patent Application No. 2018-093851 filed on May 15, 2018. The contents of those applications are incorporated herein by reference in their entireties.

What is claimed is:

1. A method for producing 1-chloro-2,3,3,4,4,5,5-heptafluoro-1-pentene, comprising:
    contacting a composition containing 1-chloro-2,3,3,4,4,5,5-heptafluoro-1-pentene and at least one substance selected from the group consisting of water, 3,3,4,4,5,5-hexafluoro-1-pentyne, 1-chloro-3,3,4,4,5,5-hexafluoro-1-pentyne and an oxide, with a solid adsorbent, to remove the at least one substance from the composition;
    wherein
    the oxide is a product obtained by reaction of 1-chloro-2,3,3,4,4,5,5-heptafluoro-1-pentene with oxygen,
    the solid adsorbent contains at least one member selected from the group consisting of an activated carbon, a zeolite, a silica and an alumina.

2. The production method according to claim 1, wherein the composition contains water, and the solid adsorbent comprises a zeolite.

3. The production method according to claim 1, wherein the composition contains at least one member selected from the group consisting of 3,3,4,4,5,5-hexafluoro-1-pentyne and 1-chloro-3,3,4,4,5,5-hexafluoro-1-pentyne, and the solid adsorbent comprises at least one member selected from the group consisting of an activated carbon and a silica.

4. The production method according to claim 1, wherein the composition contains an oxide, and the solid adsorbent is activated carbon or alumina.

5. The production method according to claim 1, wherein the oxide is at least one member selected from the group consisting of 3-chloro-2-fluoro-2-(1,1,2,2,3,3-hexafluoropropyl)-oxirane, 2,2,3,3,4,4-hexafluorobutanoyl fluoride, formyl chloride, 1-chloro-2,3,3,4,4,5,5-heptafluoro-1-hydroperoxy-1-pentene (E), 1-chloro-2,3,3,4,4,5,5-heptafluoro-1-hydroperoxy-1-pentene (Z), 1-chloro-2,3,3,4,4,5,5-heptafluoro-5-hydroperoxy-1-pentene (E) and 1-chloro-2,3,3,4,4,5,5-heptafluoro-5-hydroperoxy-1-pentene (Z).

6. The production method according to claim 1, wherein the solid adsorbent is a zeolite and the zeolite is at least one member selected from the group consisting of zeolite 3A, zeolite 4A and zeolite 5A.

7. The production method according to claim 1, wherein the solid adsorbent is an activated carbon and a specific surface area of the activated carbon is from 600 to 2,500 $m^2/g$, an average pore diameter of the activated carbon is from 1.6 to 3.5 nm and a pore volume of the activated carbon is from 0.25 to 1.5 mL/g.

8. The production method according to claim 1, wherein the solid adsorbent is a silica and the silica is porous synthetic silica gel, mesoporous silica or silica-alumina.

9. The production method according to claim 1, wherein the solid adsorbent is an alumina and a BET specific surface area of the alumina is from 50 to 350 $m^2/g$, an average pore diameter measured by a nitrogen adsorption method of the alumina is from 5 to 200 Å and a pore volume of the alumina is from 0.1 to 0.8 mL/g.

10. The production method according to claim 1, further comprising dehydrofluorination of 5-chloro-1,1,2,2,3,3,4,4-octafluoropentane to obtain the composition.

11. A composition comprising 1-chloro-2,3,3,4,4,5,5-heptafluoro-1-pentene and at least one substance selected from the group consisting of water, 3,3,4,4,5,5-hexafluoro-1-pentyne, 1-chloro-3,3,4,4,5,5-hexafluoro-1-pentyne and an oxide, wherein
    the oxide is a product obtained by reaction of 1-chloro-2,3,3,4,4,5,5-heptafluoro-1-pentene with oxygen,
    and
    the amount of said water in the composition is at most 200 mass ppm.

12. The composition according to claim 11, wherein the the composition comprises 3,3,4,4,5,5-hexafluoro-1-pentyne and an amount of the 3,3,4,4,5,5-hexafluoro-1-pentyne in the composition is from 1 to 1,200 mass ppm.

13. The composition according to claim 11, wherein the composition comprises 1-chloro-3,3,4,4,5,5-hexafluoro-1-pentyne and an amount of the 1-chloro-3,3,4,4,5,5-hexafluoro-1-pentyne in the composition is from to 600 mass ppm.

14. The composition according to claim 11, wherein the composition comprises an oxide and an amount of the oxide in the composition is from 1 to 100 mass ppm.

15. The composition according to claim 11, wherein the oxide in the composition is at least one member selected from the group consisting of 3-chloro-2-fluoro-2-(1,1,2,2,3,3-hexafluoropropyl)-oxirane, 2,2,3,3,4,4-hexafluorobutanoyl fluoride, formyl chloride, 1-chloro-2,3,3,4,4,5,5-heptafluoro-1-hydroperoxy-1-pentene (E), 1-chloro-2,3,3,4,4,5,5-heptafluoro-1-hydroperoxy-1-pentene (Z), 1-chloro-2,3,3,4,4,5,5-heptafluoro-5-hydroperoxy-1-pentene (E) and 1-chloro-2,3,3,4,5,5-heptafluoro-5-hydroperoxy-1-pentene (Z).

* * * * *